US00PP31673P2

(12) United States Plant Patent
Ammerlaan

(10) Patent No.: US PP31,673 P2
(45) Date of Patent: Apr. 14, 2020

(54) **X*GASTERALOE* PLANT NAMED 'OVROCKS06'**

(50) Latin Name: ***Aloe* hybrid x *Gasteria* hybrid**
Varietal Denomination: OVROCKS06

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 16/501,627

(22) Filed: May 13, 2019

(30) Foreign Application Priority Data

Nov. 29, 2018 (QZ) ..... PBR 2018/3123

(51) Int. Cl.
*A01H 5/00* (2018.01)

(52) U.S. Cl.
USPC ..... Plt./373

(58) Field of Classification Search
USPC ..... Plt./373
CPC ..... A01H 5/00
See application file for complete search history.

*Primary Examiner* — Annette H Para
(74) *Attorney, Agent, or Firm* — Samuel R. McCoy, Jr.

(57) ABSTRACT

A new and distinct variety of x*Gasteraloe* plant named 'OVROCKS06' which is characterized by a compact rosette of dark green foliage which is densely covered with prominent light green protuberances, as well as the stability of these characteristics from generation to generation.

4 Drawing Sheets

Latin name of the genus and species: The Latin name of the genus and species of the novel variety disclosed herein is *Aloe* hybrid x *Gasteria* hybrid which is also known by and hereinafter referred to by the nothogenus, x*Gasteraloe* hybrid Guillaumin.

Variety denomination: The inventive variety of x*Gasteraloe* disclosed herein has been given the variety denomination 'OVROCKS06'.

CROSS REFERENCE TO RELATED APPLICATIONS

This application claims priority to the Community Plant Variety Rights application number 2018/3123, filed on Nov. 29, 2018, which is herein incorporated by reference.

BACKGROUND OF THE INVENTION

Parentage: 'OVROCKS06' originated as a naturally occurring, whole-plant mutation of an unnamed x*Gasteraloe* hybrid plant (not patented). In the summer of 2016 the inventor discovered the mutation at a commercial greenhouse in Bleiswijk, the Netherlands, growing amongst a crop of the parent plant. The mutation was noted for its unique foliage and growth habit and was subsequently isolated for further evaluation in order to confirm the distinctness and stability of the characteristics first observed. Upon confirmation of distinctness and stability, 'OVROCKS06' was selected for commercialization.

Asexual Reproduction: Asexual reproduction of the new cultivar 'OVROCKS06', by way of rooting leaf cuttings, was first initiated in the summer of 2016 at the inventor's commercial greenhouse in Bleiswijk, the Netherlands. Through four subsequent generations, the unique features of this cultivar have proven to be stable and true to type.

SUMMARY OF THE INVENTION

The cultivar 'OVROCKS06' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS06'. These characteristics in combination distinguish 'OVROCKS06' as a new and distinct x*Gasteraloe* cultivar:

1. 'OVROCKS06' exhibits a compact rosette of dark green foliage; and
2. 'OVROCKS06' exhibits ovate foliage which is held upright; and
3. 'OVROCKS06' exhibits foliage which is densely covered with relatively large light green protuberances.

BOTANICAL DESCRIPTION OF THE PLANT

Figure 1:
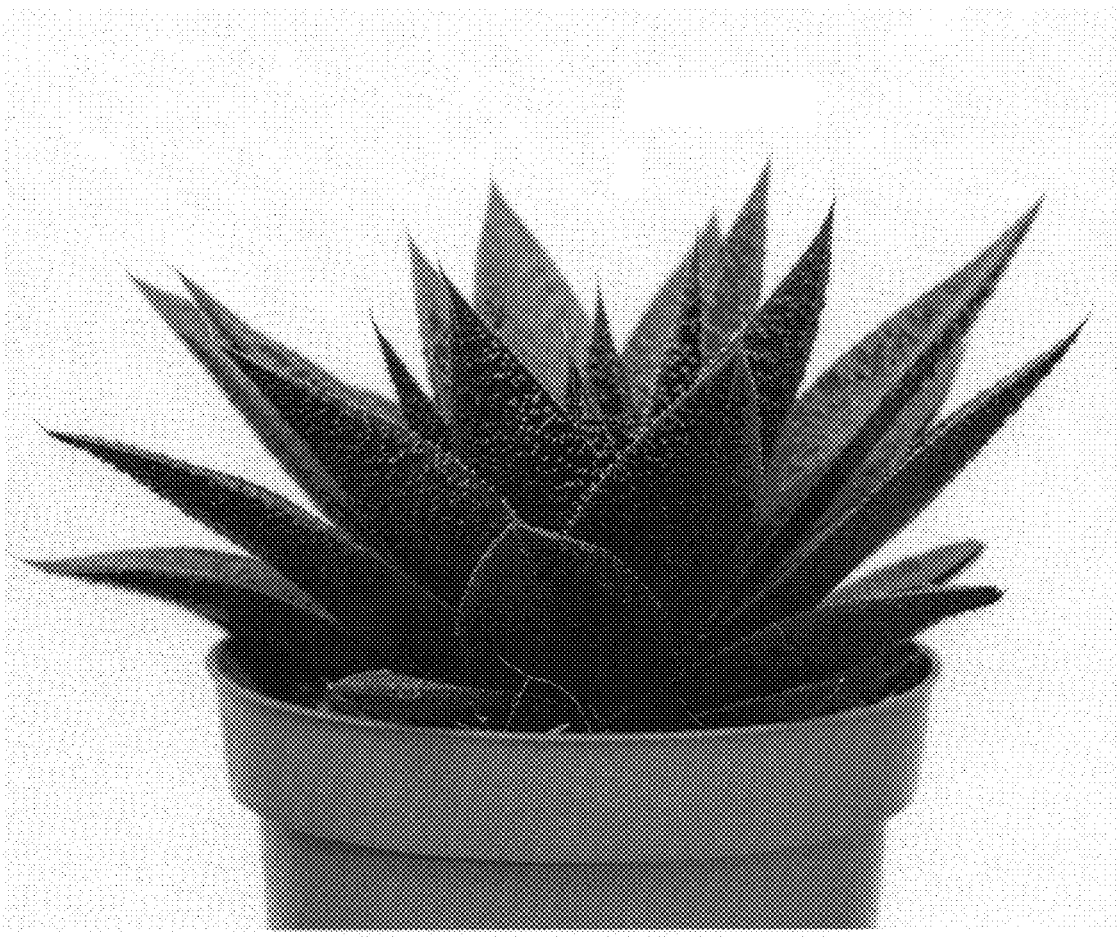
FIG. 1 illustrates, as nearly true as it is reasonably possible to make the same in color photographs of this type, an exemplary plant of 'OVROCKS06' grown in a commercial greenhouse in Bleiswijk, the Netherlands. This plant is approximately 12 months old, shown planted in a 12 cm container.
Figure 2:
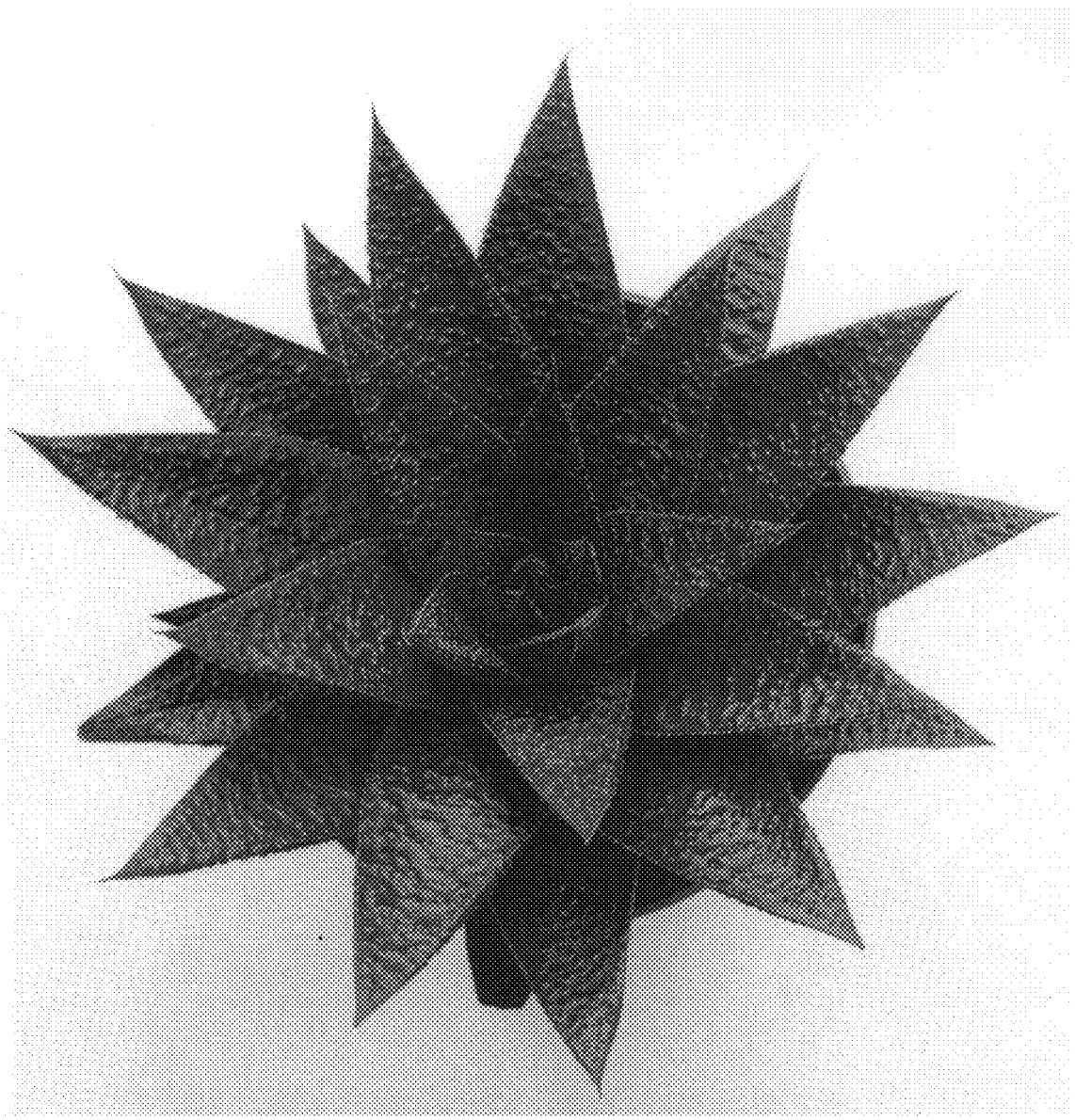
FIG. 2 illustrates, as nearly true as it is reasonably possible to make the same in color photographs of this type, the typical foliage arrangement of 'OVROCKS06'.
Figure 3:
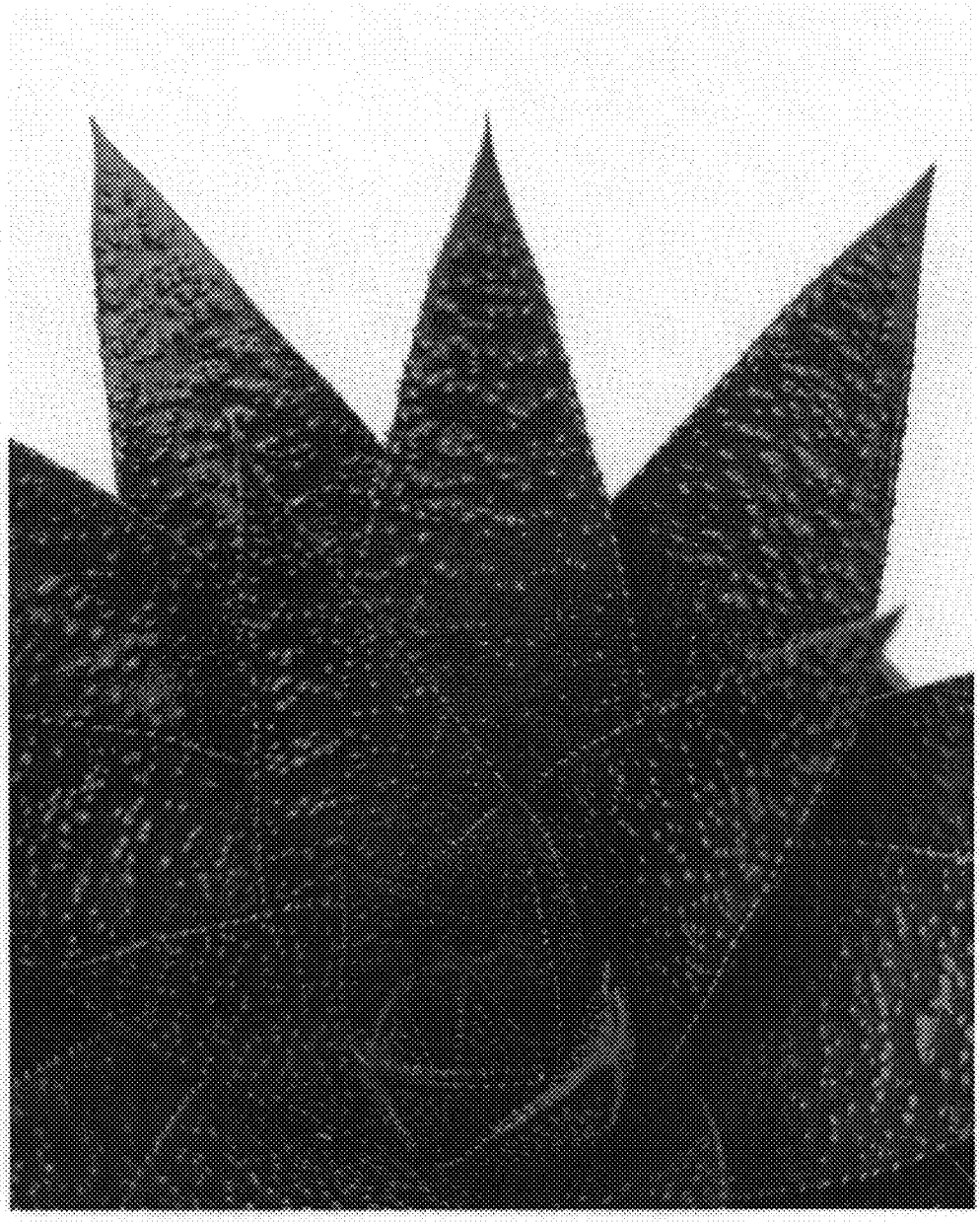
FIG. 3 illustrates, as nearly true as it is reasonably possible to make the same in color photographs of this type, the adaxial surface of the mature foliage 'OVROCKS06'.
Figure 4:
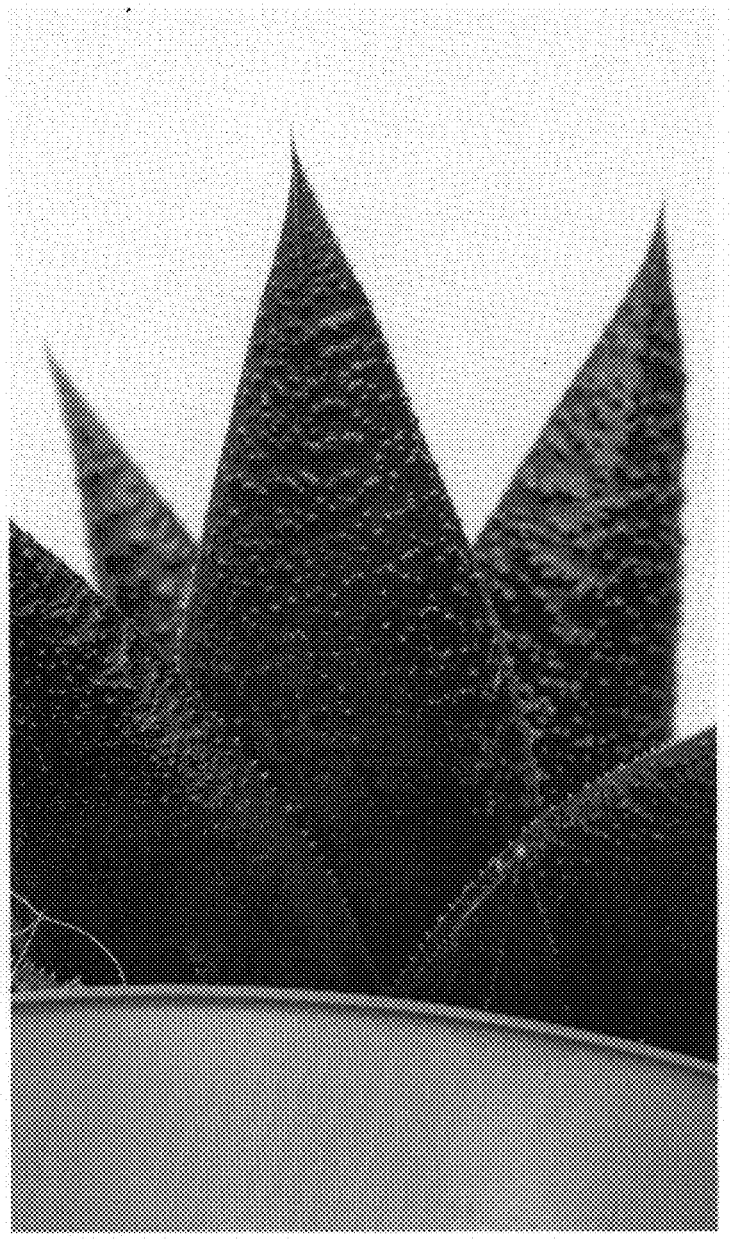
FIG. 4 illustrates, as nearly true as it is reasonably possible to make the same in color photographs of this type, the abaxial surface of the mature foliage 'OVROCKS06'.

The following observations and measurements made in June of 2017 describe averages from a sample set of six specimens of 12 months old 'OVROCKS06' plants grown in 12 cm nursery containers at commercial greenhouse in Bleiswijk, the Netherlands. Plants were produced using conventional greenhouse production protocols for x*Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS06' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS06' and a comparison with the parent and closest known comparator is provided below.

Plant description:

*Growth habit*.—Succulent perennial with foliage growing in a stemless basal rosette.

*Plant form*.—Flattened to flattened globular.

*Height from soil level to top of foliar plane*.—10.2 cm.

*Plant spread*.—Average of 18.2 cm.

*Growth rate*.—Slow to moderately fast.

*Plant vigor*.—Moderately vigorous.

*Propagation*.—Type — Leaf cuttings. Time to initiate rooting — Approximately 4 months at 21 degrees Celsius. Crop time — Approximately 14 months to produce a marketable plant in a 10.5 cm container.

*Disease and pest resistance or susceptibility*.—Neither resistance nor susceptibility to typical x*Gasteraloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a stemless, non-branching basal rosettes; no main stem or lateral branches present.

Foliage:

*Arrangement*.—Spirally placed in a rosette.

*Division*.—Simple.

*Attachment*.—Sessile.

*Quantity*.—Approximately 32 leaves per rosette.

*Shape*.—Ovate succulent leaves.

*Dimensions*.—9.8 cm long, 3.4 cm wide, and 0.8 cm thick, on average.

*Aspect*.—Slightly carinate.

*Attitude*.—At an average angle of 40 degrees to the soil level.

*Apex*.—Narrow apiculate with a soft mucronate tip.

*Base*.—Broad cuneate.

*Margin*.—Finely dentate; teeth have an average length of 0.1 cm and are colored greyed-orange, nearest to RHS 177A. Margins are not undulated or lobed.

*Texture, adaxial surface*.—Glabrous and densely covered with orbicular protuberances, each approximately 0.125 cm high and 0.125 cm in diameter.

*Texture, abaxial surface*.—Glabrous and densely covered with orbicular protuberances, each approximately 0.125 cm high and 0.125 cm in diameter. The midrib is finely dentate; teeth are approximately 0.075 cm long.

*Luster, adaxial surface*.—Moderately glossy.

*Luster, abaxial surface*.—Moderately glossy.

*Color*.—Juvenile foliage, adaxial surface — Nearest to in between green and yellow-green, RHS 139A and 147A, and fading to yellow-green towards the base, nearest to RHS 151A; leaf densely covered with protuberances which are colored greyed-green, nearest to RHS 195B. Juvenile foliage, abaxial surface — Nearest to in between green and yellow-green, RHS 139A and 147A, and fading to yellow-green towards the base, nearest to a mixture of RHS 152A and 152B; leaf densely covered with protuberances which are colored greyed-green, nearest to in between RHS 195A and 195B. Teeth along the midrib are colored greyed-orange, nearest to RHS 177B. Mature foliage, adaxial surface — Nearest to in between green and greyed-green, RHS 147B and N189A, and fading to in between purple and white towards the base, nearest to RHS 75D and N155B; leaf densely covered with protuberances which are colored yellow-green, nearest to RHS 147A, and tipped a lighter shade of yellow-green, nearest to RHS 152A. Mature foliage, abaxial surface — Nearest to in between green and greyed-green, RHS 147B and N189A, and fading to greyed-red towards the base, nearest to RHS 182D; leaf densely covered with protuberances which are colored yellow-green, nearest to RHS 147A, and tipped in between yellow-green and greyed-green, nearest to RHS 152A, 197A and 197B. Teeth along the midrib are colored greyed-orange, nearest to RHS 177A. Venation — No venation is visible.

*Petiole*.—No petiole; leaves are sessile.

Inflorescence: No flowering has been observed to date.

COMPARISONS WITH THE PARENT PLANT

Plants of the new cultivar 'OVROCKS06' differ from the parent, an unnamed x*Gasteraloe* plant hybrid (not patented), in the following characteristics described in Table 1 below.

TABLE 1

| Characteristic | 'OVROCKS06' | The parent. |
|---|---|---|
| Growth habit. | More compact. | Less compact. |
| Plant height. | Shorter than the parent. | Taller than 'OVROCKS06'. |
| General coloration of the leaf protuberances. | Light green. | Very light green-white; near white. |

COMPARISONS WITH THE CLOSEST KNOWN COMPARATOR

Plants of the new cultivar 'OVROCKS06' differ from the commercial variety, x*Gasteraloe* 'WT04' (Community Plant Variety Rights grant number 33165) in the following characteristics described in Table 2 below.

TABLE 2

| Characteristic | 'OVROCKS06' | 'WT04' |
|---|---|---|
| Foliage attitude. | More upright. | Less upright. |
| Foliage size. | Larger than WT04'. | Smaller than 'OVROCKS06'. |
| Size of the leaf protuberances | Larger than those of 'WT04'. | Smaller than 'OVROCKS06'. |
| General coloration of the leaf protuberances. | Light green. | Very light green-white; near white. |

TABLE 2-continued

| Characteristic | 'OVROCKS06' | 'WT04' |
|---|---|---|
| Foliage margins; size and prominence of teeth. | Larger than those of 'WT04'. | Smaller than those of 'OVROCKS06'. |

That which is claimed is:

1. A new and distinct variety of x*Gasteraloe* plant named 'OVROCKS06', substantially as described and illustrated herein.

* * * * *